US00PP28102P3

(12) United States Plant Patent
Jones

(10) Patent No.: US PP28,102 P3
(45) Date of Patent: Jun. 13, 2017

(54) ***DIANTHUS* PLANT NAMED 'DDTHP02-0'**

(50) Latin Name: ***Dianthus* hybrid**
Varietal Denomination: DDTHP02-0

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 14/545,916

(22) Filed: Jul. 6, 2015

(65) Prior Publication Data

US 2017/0013754 P1 Jan. 12, 2017

(51) Int. Cl.
*A01H 5/02* (2006.01)

(52) U.S. Cl.
USPC ..... Plt./272

(58) Field of Classification Search
USPC ..... Plt./272
See application file for complete search history.

*Primary Examiner* — Susan McCormick Ewoldt
(74) *Attorney, Agent, or Firm* — Cassandra Bright

(57) ABSTRACT

A new and distinct *Dianthus* cultivar named 'DDTHP02-0' is disclosed, characterized by continuous flowering on floriferous plants hardy to USDA Zone 3. Flowers are semi-double and medium pink. The new variety is a *Dianthus,* typically produced as a garden or container plant.

2 Drawing Sheets

Latin name of the genus and species: *Dianthus* hybrid.
Variety denomination: 'DDTHP02-0'.

BACKGROUND OF THE INVENTION

The new cultivar is a product of chance discovery. The new variety originated as a spontaneous whole plant mutation discovered among a commercial planting of mixed *Dianthus* hybrid varieties. The parent is unknown. 'DDTHP02-0' was discovered by the inventor, Steve Jones, at a commercial greenhouse in Santa Paula, Calif. during Spring of 2013.

Asexual reproduction of the new cultivar 'DDTHP02-0' was first performed in Santa Paula, Calif. at a commercial greenhouse by vegetative cuttings in Summer of 2013. 'DDTHP02-0' has since produced several generations and has shown that the unique features of this cultivar are stable and reproduced true to type.

SUMMARY OF THE INVENTION

The cultivar 'DDTHP02-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DDTHP02-0'. These characteristics in combination distinguish 'DDTHP02-0' as a new and distinct *Dianthus* cultivar:

1. Floriferous plants.
2. Suitability for both garden and container uses.
3. Strong medium pink flower color.
4. Continuous flowering from Spring through Fall. Repeat flowering enhanced by removal of spent flowers.
5. Hardy to USDA zone 3

COMMERCIAL COMPARISON

Plants of the new cultivar 'DDTHP02-0' are comparable to the unpatented, commercial *Dianthus* variety 'Constant Beauty Light Pink'. The two *Dianthus* varieties are similar in most horticultural characteristics; however, the new variety 'DDTHP02-0' produces a deeper pink flower. Flowers of the new variety also have a more consistent color within the same flower.

Plants of the new cultivar 'DDTHP02-0' can also be compared to the unpatented, commercial *Dianthus* variety 'Kahori'. These varieties are similar in most horticultural characteristics; however 'DDTHP02-0' produces a semi double, pink colored flower, whereas comparator 'Kahori' produces a single form flower of a deeper pink color. 'DDTHP02-0' is shorter in height; up to 25 cm compared to 35 cm of comparator 'Kahori'. 'DDTHP02-0' also has a perpetual flowering habit, whereas comparator 'Kahori' flowers only in the spring.

BRIEF DESCRIPTION OF THE PHOTOGRAPHS

Figure 1:
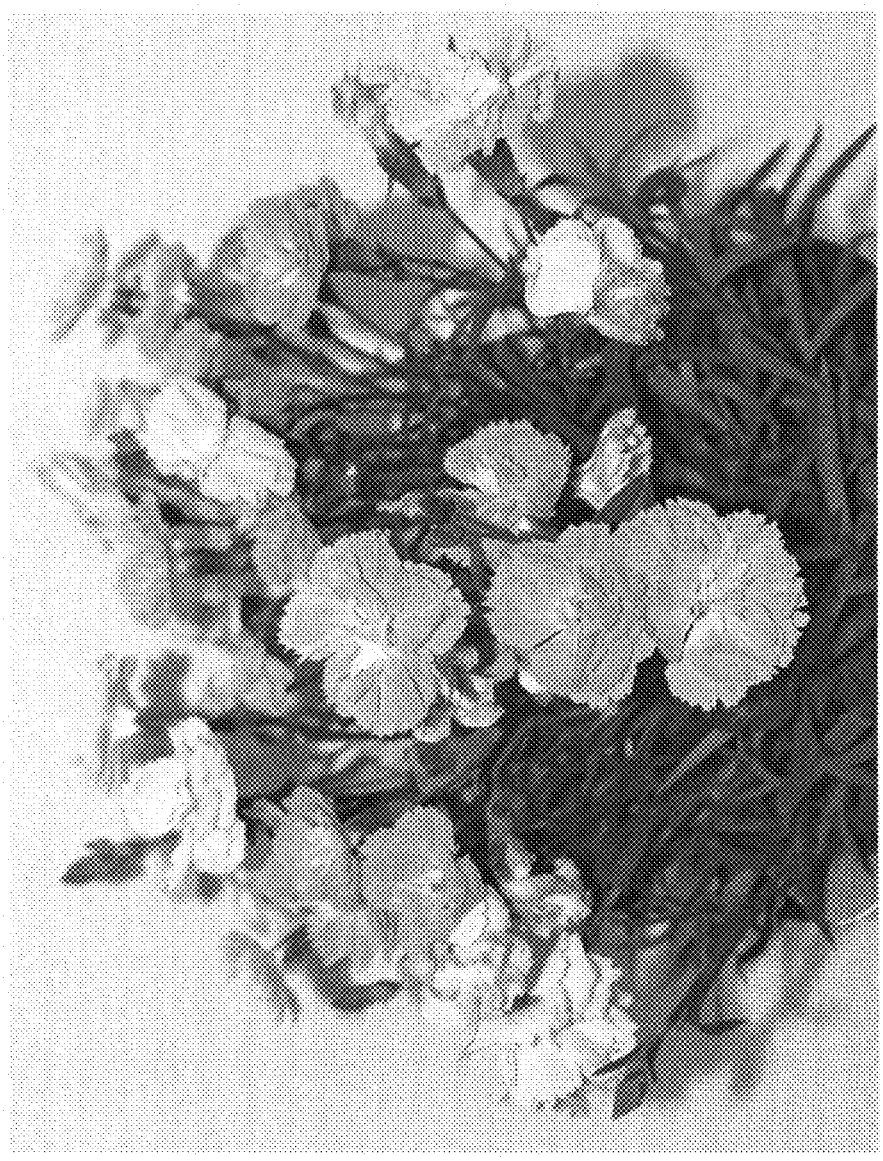

The accompanying photograph in FIG. 1 illustrates in full color a typical plant of 'DDTHP02-0' grown outdoors in Santa Paula, Calif. This plant is approximately 17 weeks old, shown in a 8 inch pot.

Figure 2:
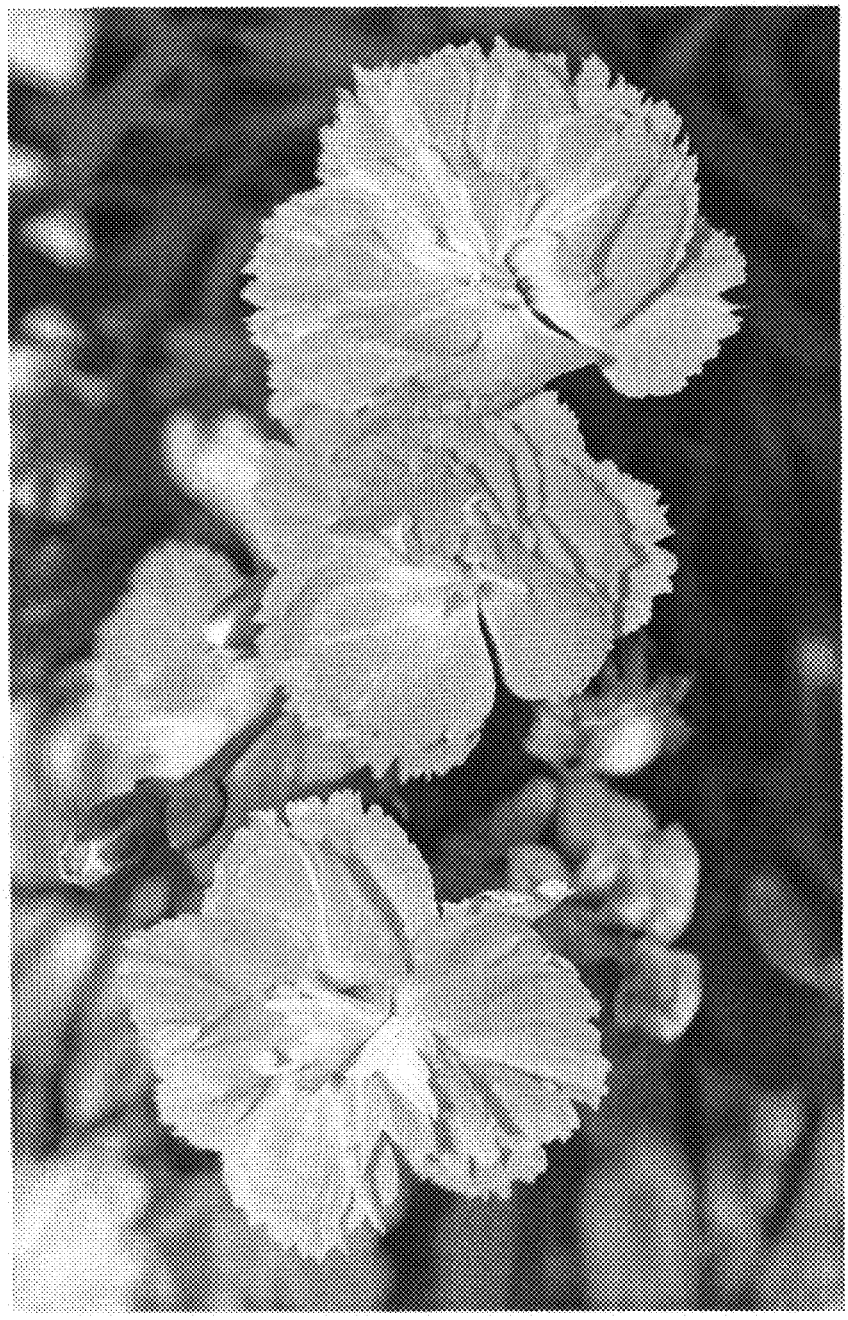

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2007, except where general terms of ordinary dictionary significance are used. The following observations and measurements describe 'DDTHP02-0' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light.

Measurements and numerical values represent averages of typical plant types.

Botanical classification: *Dianthus* hybrid 'DDTHP02-0'.

PROPAGATION

Time to initiate roots: About 10 days at approximately 24° C.

Time to produce a rooted cutting: About 18 days at 24° C.

Root description: Fibrous roots, approximately 1 to 3 mm in diameter, colored near Orange-White 159C.

PLANT

Age of plant described: Approximately 20 weeks from rooted cutting.

Pot size: 1 gallon.

Plant type: Compact upright perennial.

Plant habit: Upright growing stems emerge basally.

Plant spread: Approximately 25 cm.

Height: Approximately 20 cm to top of flowering plane. Approximately 12 cm to top of foliar plane.

Length plant stem: Average range 10 to 14 cm.

Diameter of plant stem: Approximately 0.4 cm.

Quantity stems: Approximately 40.

Stem:

*Color.*—Near RHS Green 136B.

*Texture.*—Smooth.

Internode length: Average 4 cm.

Stem hollowness: Approximately 90% solid.

FOLIAGE

Leaf:

*Arrangement.*—Opposite (in pairs).

*Quantity.*—Approximately 4-6 fully expanded per stem. Average range of 8 to 10 immature leaves per stem.

*Average length.*—Approximately 5.7 cm.

*Average width.*—Approximately 0.6 cm.

*Shape of blade.*—Linear.

*Apex.*—Acute.

*Base.*—Clasping.

*Attachment.*—Sessile.

*Margin.*—Entire.

*Texture of top surface.*—Smooth.

*Texture of bottom surface.*—Smooth.

*Pubescence.*—None.

*Color.*—Young foliage upper side: Near RHS Green 139A. Young foliage under side: Near RHS Green 137A. Mature foliage upper side: Between RHS Green 136A and 137A. Mature foliage under side: Near RHS Green 139A.

*Venation.*—Type: Linear with a prominent mid vein. Venation color upper side: Indistinguishable from foliage. Venation color under side: Indistinguishable from foliage.

FLOWER

Natural flowering season: Perpetual flowering.

Inflorescence type and habit: Umbel of 2 flowers, or single occurring flowers.

Flower longevity on plant: 2-3 weeks.

Quantity of flowers: Approximately 40 flowers on a 20 week old plant.

Flowers persistent or self cleaning: Persistent.

Fragrance: Noticeable sweet scent.

Inflorescence size:

*Diameter.*—Approximately 5.5 cm.

*Height.*—Approximately 7.0 cm.

Individual flower size:

*Diameter.*—Approximately 3.8 cm.

*Length.*—Approximately 3.9 cm.

Petals, excluding tube:

*Petal arrangement.*—Whorled, multiple whorl.

*Shape.*—Spatulate, with an elongated narrow base and orbicular distal section.

*Base.*—Attenuate.

*Margin.*—Serrated.

*Apex.*—Sharply serrated or notched.

*Length.*—2.8 cm.

*Width.*—1.8 cm.

*Petal quantity.*—Average 15.

*Texture.*—Smooth all surfaces.

*Aspect.*—Flat to slightly undulating.

*Color.*—When opening: Upper surface: Near RHS Purple 77B. Base near White N155B. Lower surface: Near RHS Purple-Violet, N82B and N82C. Base near White N155B. Fully opened: Upper surface: Between Purple 76A and Purple 77A. Base near White N155B. Lower surface: Near RHS Purple 76A. Base near White N155B.

*Fading.*—Upper surface: Near RHS Purple 76B. Base near White N155B. Lower surface: Near RHS Purple 76D. Base near White N155B.

Tube:

*General description.*—Tube consists of the elongated, unfused base of the petals. Tube shape caused by a fused calyx. Length: 2.3 cm. Width: 0.7 cm. Texture: Smooth.

*Color.*—When opening: Inner surface: Near RHS group Greyed-Green 191A. Outer surface: Near RHS Green 137C. Fully opened: Inner surface: Near RHS group Greyed-Green 191A. Outer surface: Near RHS Green 137C. Fading: Upper surface: No change. Lower surface: No change.

Bud:

*Shape.*—Elongated cylinder, with minimal extrusion of styles.

*Length.*—Average 2.5 cm.

*Diameter.*—Average 0.8 cm.

*Color.*—Near RHS Greyed-Green 191A.

Sepals:

*Quantity.*—5.

*Arrangement.*—Fused tube.

*Shape.*—Cynlindric.

*Length.*—2.3 cm.

*Width.*—0.7 cm.

*Margin.*—Entire.

*Apex.*—Acute.

*Texture.*—Smooth upper and lower surfaces.

*Color.*—Near RHS Greyed-Green 191A.

Bracteoles:
*Shape.*—Deltate.
*Quantity per flower.*—4.
*Length.*—Approximately 0.6 cm.
*Width.*—Approximately 0.3 cm.
*Margin.*—Entire.
*Texture.*—Smooth.
*Color.*—Near RHS Green 137D.

Peduncle:
*Length.*—Average 2.5 cm.
*Diameter.*—0.2 cm.
*Color.*—Near RHS group Greyed-Green 191A.
*Orientation.*—Upright.
*Strength.*—Flexible.
*Texture.*—Smooth.

Pedicel:
*Length.*—Average 2.5 cm.
*Diameter.*—0.15 cm.
*Color.*—Near RHS group Greyed-Green 191A.
*Orientation.*—Upright.
*Strength.*—Flexible, elastic.

REPRODUCTIVE ORGANS

Stamens:
*Number.*—2, 4 or 6. Variable.
*Filament length.*—Approximately 2.5 cm.

Anthers:
*Shape.*—Oblong.
*Length.*—Approximately 0.3 cm.
*Color.*—Near RHS Greyed-Purple N187D.
*Pollen.*—Not observed.

Pistil:
*Number.*—2.
*Length.*—Approximately 3.1 cm.
*Style.*—Length: Approximately 2.3 cm. Color: Near RHS Purple 76D.

Stigma:
*Shape.*—Linear, arching.
*Color.*—Near RHS Purple 76D.
*Ovary shape.*—Oblong.
*Ovary diameter.*—0.3 cm.
*Ovary length.*—0.7 cm.
*Ovary color.*—Near RHS Green-White 157A.

OTHER CHARACTERISTICS

Seeds and fruits: Not observed to date.

Disease/pest resistance: Neither resistance nor susceptibility to the normal diseases and pests of *Dianthus* has been observed. Typical diseases of *Dianthus* include: *Alternaria dianthicola, Botrytis cinerea,* and *Uromyces dianthi,* Typical pests include; various species of Thysanopthera, and various *Aphid* species.

Temperature tolerance: USDA zone 3 through 10 tolerant.

What is claimed is:

1. A new and distinct cultivar of *Dianthus* plant named 'DDTHP02-0' as herein illustrated and described.

* * * * *